United States Patent
Hatcher

(10) Patent No.: US 8,167,482 B2
(45) Date of Patent: May 1, 2012

(54) THERMOGRAPHY INSPECTION OF SURFACE DISCONTINUITIES

(75) Inventor: Clifford Hatcher, Orlando, FL (US)

(73) Assignee: Siemens Energy, Inc., Orlando, FL (US)

( * ) Notice: Subject to any disclaimer, the term of this patent is extended or adjusted under 35 U.S.C. 154(b) by 393 days.

(21) Appl. No.: 12/498,659

(22) Filed: Jul. 7, 2009

(65) Prior Publication Data

US 2011/0007774 A1  Jan. 13, 2011

(51) Int. Cl.
*G01N 25/00* (2006.01)
*G01K 1/00* (2006.01)
(52) U.S. Cl. .................... 374/4; 374/7; 374/45; 374/120
(58) Field of Classification Search .................. 374/4, 7, 374/45, 120
See application file for complete search history.

(56) References Cited

U.S. PATENT DOCUMENTS

| | | | |
|---|---|---|---|
| 3,830,094 A * | 8/1974 | Leger | 374/5 |
| 4,314,474 A * | 2/1982 | Dermarderosian | 374/4 |
| 4,430,897 A * | 2/1984 | Quate | 73/606 |
| 6,488,405 B1 * | 12/2002 | Eppes et al. | 374/5 |
| 7,084,402 B2 | 8/2006 | Thompson | |
| 7,287,902 B2 | 10/2007 | Safai et al. | |
| 7,432,505 B2 | 10/2008 | Brummel | |
| 7,513,682 B2 * | 4/2009 | McClure et al. | 374/5 |

FOREIGN PATENT DOCUMENTS

JP  01295148 A  * 11/1989

OTHER PUBLICATIONS

Translation of JP01295148A.*

* cited by examiner

*Primary Examiner* — Lisa Caputo
*Assistant Examiner* — Mirellys Jagan

(57) ABSTRACT

A method for detecting surface discontinuities in a test specimen. The method includes applying a one or more substances including a detection medium to the test specimen wherein the detection medium enters at least one surface discontinuity in the test specimen. The specimen surface is monitored for discontinuity signatures produced by the detection medium. The monitoring includes monitoring the detection medium to detect a temperature differential indicative of a surface discontinuity in the test specimen wherein the discontinuity signatures include a warm signature emitted by the detection medium that has entered the surface discontinuity.

11 Claims, 4 Drawing Sheets

THERMOGRAPHY INSPECTION OF SURFACE DISCONTINUITIES

FIELD OF THE INVENTION

This invention relates generally to non-destructive inspection methods and, more particularly, to inspection methods that use an endothermic or exothermic reaction at a discontinuity to detect the discontinuity using thermography.

BACKGROUND OF THE INVENTION

Maintaining the structural integrity of certain structures is very important in many fields because of safety concerns, downtime, cost, etc. Loss of structural integrity is typically caused by material defects, such as cracks, disbonds, corrosion, voids, etc. that may exist in or on the structure. For example, it is important in the power generation industry that reliable techniques are available to examine the structural integrity of turbine engine, generator and other plant equipment to ensure the components and systems do not suffer failure during operation. In particular, the structural integrity of turbine blades and rotors requires monitoring through inspections to facilitate the long term service life of the turbine engine. A common method for detection of a crack or defect is visual examination by skilled personnel. However, it is known that cracks or defects that may affect the integrity of structural components may not be readily visible without the use of special techniques to aid the examiner. Therefore, various techniques have been developed in the art for non-invasive and non-destructive analysis of different structural components and materials in various industries.

SUMMARY OF THE INVENTION

In accordance with one aspect of the invention, a method is provided for detecting surface discontinuities in a test specimen, the method comprising: applying a liquid detection medium to the test specimen wherein the liquid detection medium enters at least one surface discontinuity in the test specimen through capillary action; and monitoring the surface of the test specimen for discontinuity signatures produced by the liquid detection medium including monitoring the liquid detection medium to detect a temperature differential indicative of a surface discontinuity in the test specimen; wherein the discontinuity signatures comprise a warm signature emitted by the liquid detection medium that has entered the surface discontinuity.

The temperature signature may be determined by detecting the warm signature relative to a cooler signature measured on an area of the test specimen surrounding the surface discontinuity.

The warm signature may comprise the result of an endothermic reaction following application of the liquid detection medium to the test specimen.

The endothermic reaction may comprise evaporation of the liquid detection medium from the area of the test specimen surrounding the surface discontinuity at a faster rate than evaporation of the liquid detection medium that has entered the surface discontinuity.

The liquid detection medium may comprise a volatile liquid, and may comprise at least one of alcohol, acetone and ethylene.

The warm temperature signature may comprise the result of an exothermic reaction following application of the liquid detection medium to the test specimen, and the exothermic reaction may be produced by applying a reacting medium to the liquid detection medium.

The liquid detection medium may be substantially removed from an area surrounding the surface discontinuity prior to application of the reaction medium, and the reaction medium may be applied to an area including both the surface discontinuity and the area surrounding the surface discontinuity.

One of the liquid detection medium and the reaction medium may be chemically alkaline, and the other of the liquid detection medium and the reaction medium may be chemically acidic.

The temperature signatures may be produced on the test specimen without application of an excitation energy to the test specimen.

The monitoring may comprise thermally monitoring the liquid detection medium by acquiring infrared images of the test specimen and liquid detection medium.

The discontinuity may be a crack formed in the surface of the test specimen.

In accordance with another aspect of the invention, a method is provided for detecting surface discontinuities in a test specimen without application of an external excitation energy to the specimen, the method comprising: applying a detection medium to the test specimen wherein the detection medium enters at least one surface discontinuity in the test specimen; and monitoring the surface of the test specimen for discontinuity signatures produced by the detection medium including monitoring the detection medium to detect a temperature differential indicative of a surface discontinuity in the test specimen; wherein the discontinuity signatures comprise a warm signature emitted by the detection medium that has entered the surface discontinuity, and the warm signature is detected relative to a cooler signature measured on an area of the test specimen surrounding the surface discontinuity.

BRIEF DESCRIPTION OF THE DRAWINGS

While the specification concludes with claims particularly pointing out and distinctly claiming the present invention, it is believed that the present invention will be better understood from the following description in conjunction with the accompanying Drawing Figures, in which like reference numerals identify like elements, and wherein:

DETAILED DESCRIPTION OF THE INVENTION

In the following detailed description of the preferred embodiment, reference is made to the accompanying drawings that form a part hereof, and in which is shown by way of illustration, and not by way of limitation, specific preferred embodiments in which the invention may be practiced. It is to be understood that other embodiments may be utilized and that changes may be made without departing from the spirit and scope of the present invention.

According to one aspect, the invention provides methods for detecting surface discontinuities in a component or test specimen, such as a component for use in turbo-machinery (e.g. gas or steam turbines). Surface discontinuities detected by the methods of the invention may in particular comprise, for example, linear cracks, porosity, etc, or similar discontinuities that may characterize a defect formed or located on the surface of a component or test specimen. The methods provide an active thermography technique in which one or more chemicals may be applied to the surface of the specimen, the chemical or chemicals produce a reaction to provide an indication to a thermal imaging device of a surface discontinuity location without application of an external excitation energy.

Figure 1:
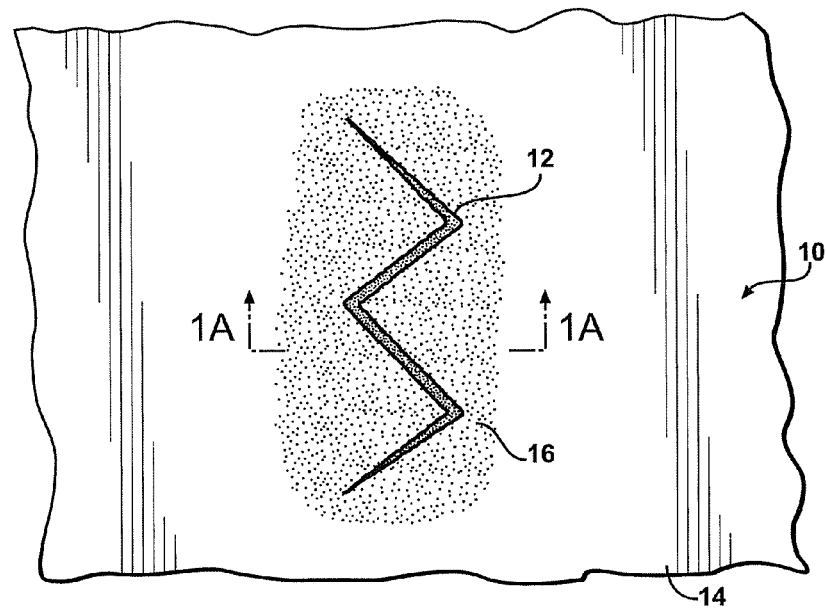
FIG. 1 is a schematic plan view illustrating an enlarged section of a test specimen coated with a detection medium in accordance with a step of a first embodiment of the invention.

FIG. 1 illustrates a component or test specimen 10 in accordance with a first embodiment of the invention. A surface discontinuity is indicated by reference numeral 12 and extends inwardly from a surface 14 of the specimen 10, see FIG. 1A. In an initial step of the method of the present embodiment, a liquid detection medium 16 is applied to at least a portion of the surface 14 to be monitored. The liquid detection medium 16 is applied to substantially coat the surface 14 as well as to transport into the discontinuity 12, such as through capillary action drawing the liquid detection medium 16 into a subsurface cavity 18 defined by the discontinuity 12. That is, the adhesion of the liquid detection medium 16 to the inwardly extending surfaces of the cavity 18 interacts with the surface tension of the liquid to cause the liquid detection medium 16 to move into the cavity 18. The liquid detection medium 16 may be applied by any known technique to substantially wet the specimen surface 14 with the detection medium 16, with sufficient liquid being applied to cause the liquid detection medium 16 to transport under capillary action into the discontinuity 12 to fill the cavity 18.

The liquid detection medium 16 in accordance with the first embodiment comprises a chemical substance that readily produces an endothermic reaction on the surface 14. In particular, the liquid detection medium 16 preferably comprises a volatile liquid, i.e., a liquid that readily vaporizes or evaporates at approximately room temperature (approximately 22° C.). For example, the liquid detection medium 16 may comprise, without limitation, alcohol, acetone or ethylene. The liquid detection medium 16 is preferably selected with reference to the material of the specimen 10, such that the liquid detection medium 16 does not cause deterioration of the specimen 10 through contact with the surface 14 or within the cavity 18.

Figure 1A:
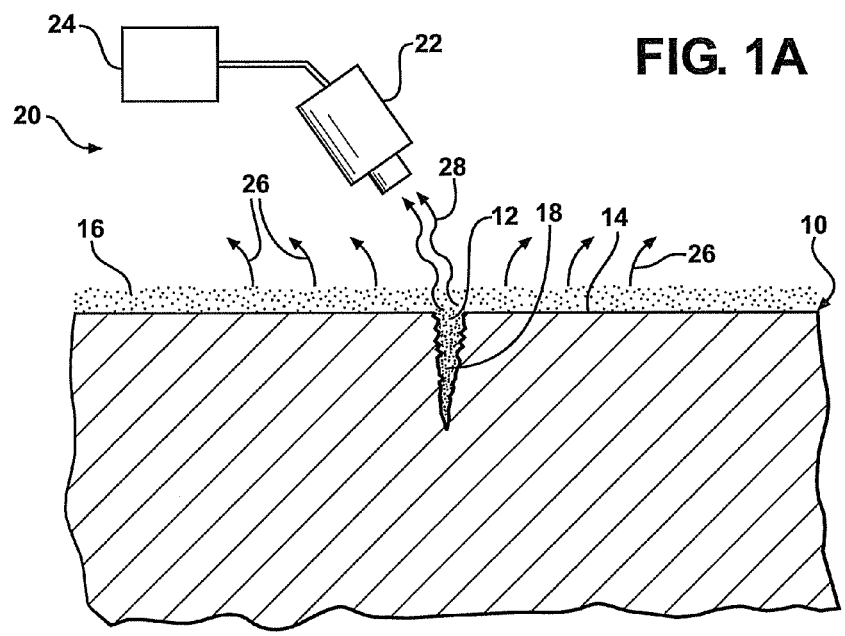
FIG. 1A is an enlarged cross sectional view taken along line 1A-1A in FIG. 1, and illustrating a monitoring step for detecting a surface discontinuity in accordance with the first embodiment of the invention.

As seen in FIG. 1A, a system 20 for implementing the present invention includes a thermal imaging device, depicted herein as comprising an infrared camera 22 directed at the surface 14 and connected to a display screen 24 capable of displaying thermal images acquired by the infrared camera 22, whereby real-time images may be displayed to an observer or inspector to determine the location and characteristics of the discontinuity. Alternatively, in place of the display screen 24, a digital processor may be provided connected to the camera 22, e.g., a digital camera, for implementing the discontinuity detection method in an automated system, such as for implementing a computer-aided non-destructive examination process. A computer-aided examination process for the present method may comprise computer software implementation of known auto-defect recognition techniques.

In a step of monitoring the surface 14 to detect the surface discontinuity 12, the camera 22 acquires thermal images of the surface 14 following application of the liquid detection medium 16. The thermal images comprise discontinuity signatures where an endothermic reaction of the liquid detection medium 16 on the surface 14, due to vaporization or evaporation (indicated by arrows 26), produces a temperature differential relative to an endothermic reaction of the liquid detection medium 16 present within the discontinuity 12. Specifically, the liquid detection medium 16 within the discontinuity 12 has a greater volume and will evaporate more slowly than the liquid detection medium on the surface 14. Hence, the discontinuity signature acquired by the camera 22 corresponds to a lower frequency infrared emission 28 from the discontinuity 12 and will appear as a warm signature relative to the area of the surface 14 surrounding the discontinuity 12, where the liquid detection medium 16 has a lower volume and will evaporate more quickly to create a cooler temperature signature.

The system 20 is substantially sensitive to small temperature changes. In particular, the camera 22 is capable of detecting changes at least as small as approximately 0.5° C., and preferably comprises a detection capability of approximately 10 millikelvin. Accordingly, although the discontinuity 12 being detected may be small, e.g., a crack, with a correspondingly small volume for the cavity 18 to receive the liquid detection medium 16, the additional volume of the cavity 18 is sufficient to provide a detectable warm signature relative to the temperature signature of the surrounding surface 14. Since the discontinuity signature provided by the temperature differential, and associated temperature signatures, of the discontinuity 12 and the surrounding surface 14 are produced by an endothermic reaction of the liquid detection medium 16, no additional energy input to the specimen, such as by ultrasonic stimulation of the specimen 10 or heat input to the specimen 10, is required to provide measurable results for locating the discontinuity 12 using the present system 20.

Figure 2:
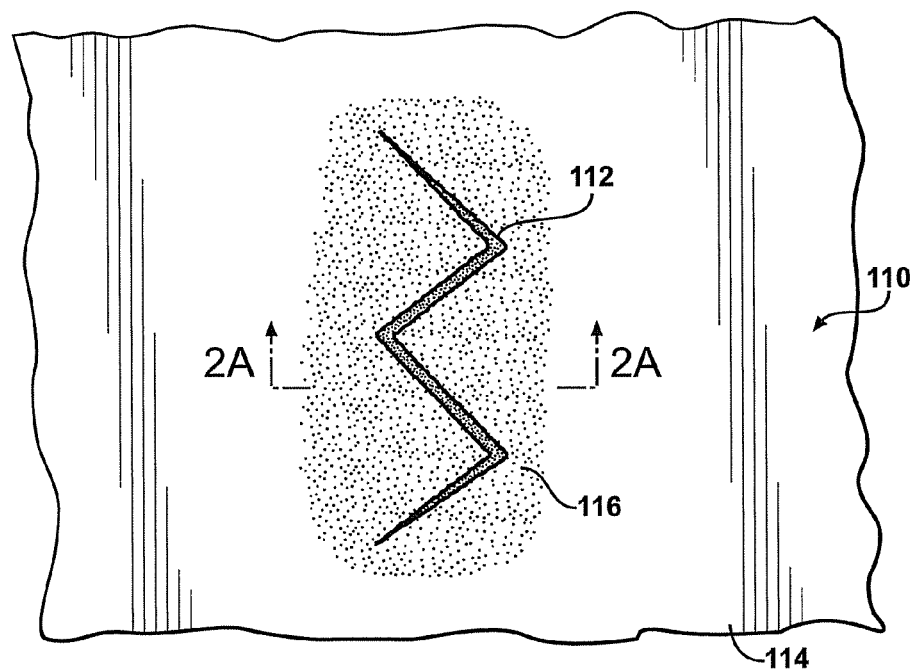
FIG. 2 is a schematic plan view illustrating an enlarged section of a test specimen coated with a detection medium in accordance with a step of a second embodiment of the invention.
Figure 2A:
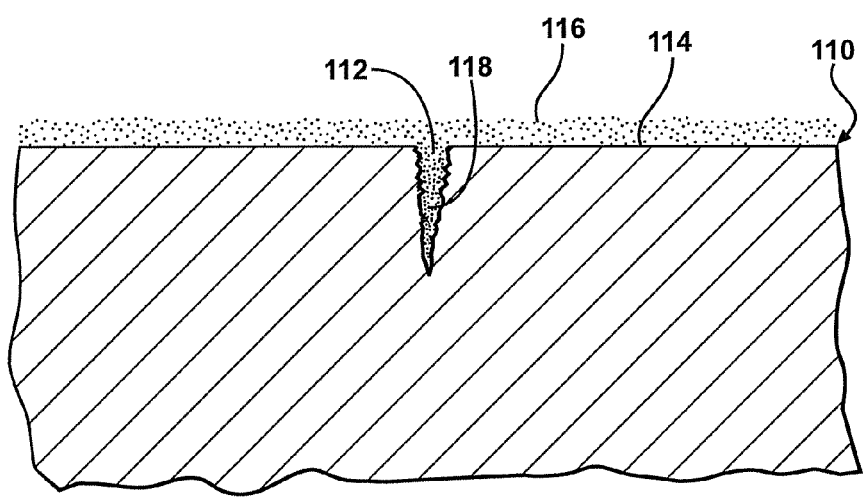
FIG. 2A is an enlarged cross sectional view taken along line 2A-2A in FIG. 2.

FIG. 2 illustrates a component or test specimen 110 in accordance with a second embodiment of the invention. A surface discontinuity is indicated by reference numeral 112 and extends inwardly from a surface 114 of the specimen 110, see FIG. 2A. As in the previous embodiment, in an initial step of the method of the present embodiment, a detection medium 116 is applied to substantially coat at least a portion of the surface 114 to be monitored as well as to transport into the discontinuity 112. For example, the detection medium 116 may be a liquid detection medium and may transport into the discontinuity 112 through capillary action drawing the detection medium 116 into a subsurface cavity 118 defined by the discontinuity 112. The detection medium 116 may be applied by any known technique to substantially cover at least a portion of the specimen surface 114 to be monitored with the detection medium 116, with sufficient liquid being applied to cause the detection medium 116 to transport under capillary action into the discontinuity 112 to fill the cavity 118.

Figure 3:
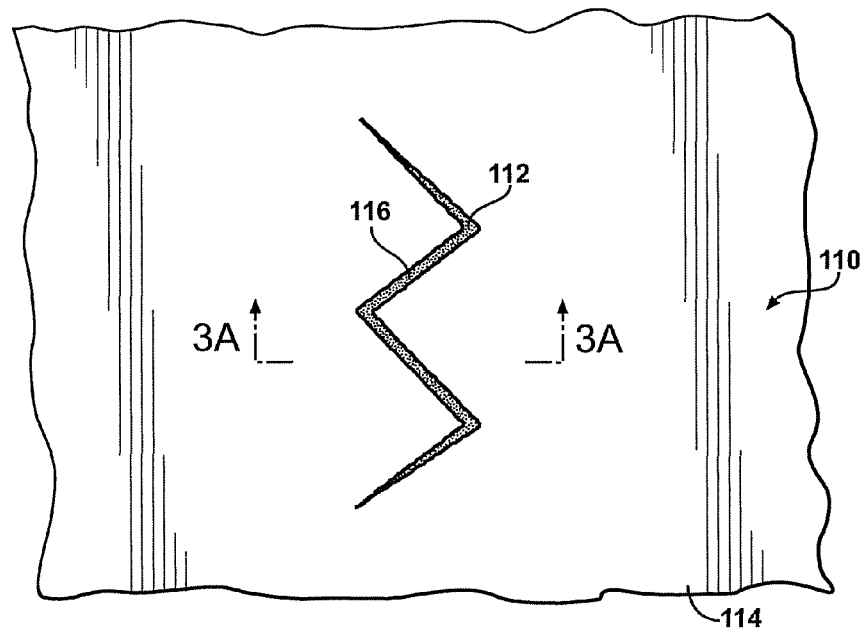
FIG. 3 is a schematic plan view illustrating the test specimen of FIG. 2 in which a residual amount of the first detection medium surrounding a surface discontinuity has been removed in accordance with a step of the second embodiment of the invention.
Figure 3A:
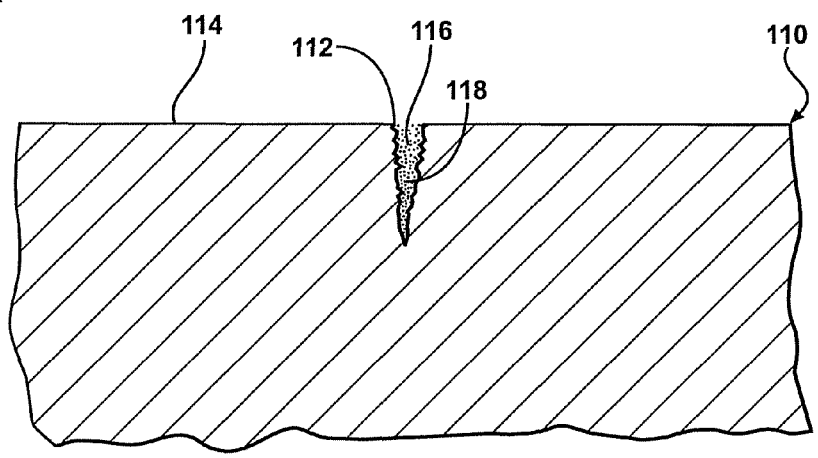
FIG. 3A is an enlarged cross sectional view taken along line 3A-3A in FIG. 3.

Following application of the detection medium 116 to the surface 114, and entry of the liquid detection medium into the cavity 118 of the discontinuity 112, the detection medium 116 is wiped or substantially removed from the surface 114, such that only the detection medium 116 within the cavity 118 remains, as is illustrated in FIGS. 3 and 3A.

Figure 4:
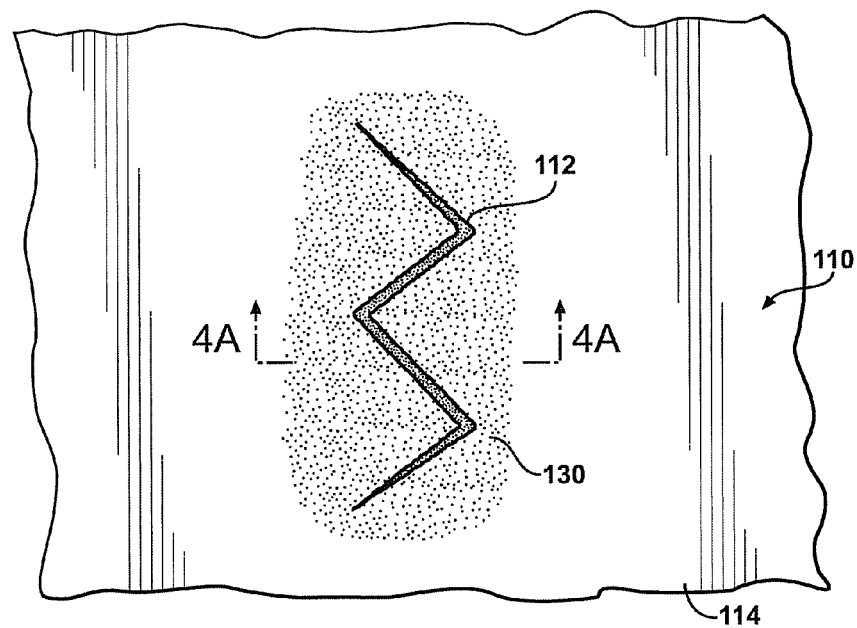
FIG. 4 is a schematic plan view illustrating the test specimen of FIG. 2 coated with a reacting medium in accordance with a step of the second embodiment of the invention.

Referring to FIG. 4, a reacting medium 130 is applied to the same portion of the specimen surface 114 that previously received the application of the detection medium 116. The reacting medium 130 may be applied by any known technique to cover a substantial portion of the surface surrounding the discontinuity 112, as well as to enter the cavity 118.

The detection medium 116 and the reacting medium 130 comprise different chemical substances that mix and react with each other to produce an exothermic reaction. For example, one of the detection medium 116 and the reacting medium 130 may comprise a substance that is chemically alkaline, and the other of the detection medium 116 and the reacting medium 130 may comprise a substance that is chemically acidic. Further, one of the detection medium 116 and the reacting medium 130 may be a liquid, and the other of the detection medium 116 and the reacting medium 130 may comprise either a liquid or a solid, e.g., a powder. The detection medium 116 and the reacting medium 130 are preferably selected with reference to the material of the specimen 110, such that the detection medium 116 and reacting medium 130 do not cause deterioration of the specimen 110 through contact with the surface 114 or within the cavity 118.

Figure 4A:
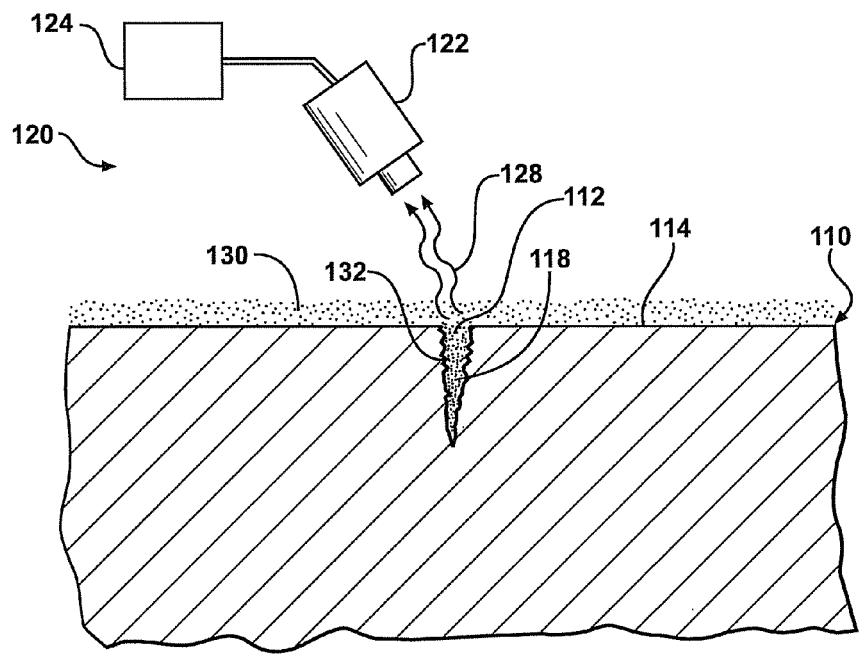
FIG. 4A is an enlarged cross sectional view taken along line 4A-4A in FIG. 4, and illustrating a monitoring step for detecting a surface discontinuity in accordance with the second embodiment.

As seen in FIG. 4A, a system 120 for implementing the present invention includes a thermal imaging device. As with the previous embodiment, the thermal imaging device may comprise an infrared camera 122 directed at the surface 114 and connected to a display screen 124 capable of displaying thermal images acquired by the infrared camera 122, whereby real-time images may be displayed to an observer or inspector to determine the location and characteristics of the surface discontinuity. Alternatively, in place of the display screen 124, a digital processor may be provided connected to the camera 122, e.g., a digital camera, for implementing the surface discontinuity detection method in an automated system, such as for implementing a computer-aided non-destructive examination process.

In a step of monitoring the surface 114 to detect the discontinuity 112, the camera 122 acquires thermal images of the surface 114 following application of the reacting medium 130. In particular, upon application of the reacting medium 130 to the surface 114, at least a portion of the reacting medium 130 will enter the cavity 118 and mix or interact with the detection medium 116, as indicated at 132. The interaction of the detection medium 116 and the reacting medium 130 comprises an exothermic reaction at the location of the discontinuity 112, and defines a temperature differential relative to the portion of the surface 114 surrounding the discontinuity 112. The thermal images acquired by the camera 122 comprise discontinuity signatures of the exothermic reaction at the discontinuity 112 relative to the surface 114 surrounding the discontinuity 112. In particular, the discontinuity signature acquired by the camera 122 corresponds to a lower frequency infrared emission 128 from the discontinuity 112 and will appear as a warm signature relative to the area of the surface 114 surrounding the discontinuity 112, where the detection medium 116 has been substantially removed and no reaction occurs upon application of the reacting medium 130, to provide a cooler temperature signature surrounding the discontinuity 112.

Since the discontinuity signature provided by the temperature differential, and associated temperature signatures, of the discontinuity 112 and the surrounding surface 114 are produced by an exothermic reaction of the detection medium 116 reacting with the reacting medium 130, no additional energy input to the specimen, such as, for example, ultrasonic stimulation of the specimen 110 or heat input to the specimen 110, is required to provide measurable results for locating the discontinuity 112 using the present system 120.

From the above description, it should be apparent that the present invention provides a method of detecting a discontinuity on a specimen through a readily implemented chemical surface treatment, providing a sensitive thermal imaging indication of the discontinuity.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for detecting surface discontinuities in a surface of a test specimen, the method comprising:
    applying a liquid detection medium to the test specimen wherein the liquid detection medium enters at least one surface discontinuity in the test specimen through capillary action; and
    monitoring the surface of the test specimen for discontinuity signatures produced by the liquid detection medium including monitoring the liquid detection medium to detect a temperature differential indicative of a surface discontinuity in the test specimen;
    wherein the discontinuity signatures comprise a warm signature emitted by the liquid detection medium that has entered the surface discontinuity and which is detected relative to an area of the test specimen surrounding the surface discontinuity; and
    the warm signature comprises the result of an exothermic reaction following application of the liquid detection medium to the test specimen.

2. The method of claim 1, wherein the discontinuity signatures are produced on the test specimen without application of an excitation energy to the test specimen.

3. The method of claim 1, wherein the monitoring comprises thermally monitoring the liquid detection medium by acquiring infrared images of the test specimen and liquid detection medium.

4. The method of claim 1, wherein the discontinuity comprises a crack in the surface of the test specimen.

5. The method of claim 1, including applying a reacting medium to the liquid detection medium to produce the exothermic reaction.

6. The method of claim 5, wherein the liquid detection medium is substantially removed from an area surrounding the surface discontinuity prior to application of the reacting medium, and the reacting medium is applied to an area including both the surface discontinuity and the area surrounding the surface discontinuity.

7. The method of claim 5, wherein one of the liquid detection medium and the reacting medium is chemically alkaline, and the other of the liquid detection medium and the reacting medium is chemically acidic.

8. A method for detecting surface discontinuities in a surface of a test specimen without application of an external excitation energy to the specimen, the method comprising:

applying a detection medium to the test specimen wherein the detection medium enters at least one surface discontinuity in the test specimen; and monitoring the surface of the test specimen for discontinuity signatures produced by the detection medium including monitoring the detection medium to detect a temperature differential indicative of a surface discontinuity in the test specimen;

wherein the discontinuity signatures comprise a warm signature emitted by the detection medium that has entered the surface discontinuity, and the warm signature is detected relative to a cooler signature measured on an area of the test specimen surrounding the surface discontinuity; and the warm signature comprises the result of an exothermic reaction, and including application of a reacting medium to the detection medium to produce the exothermic reaction.

9. The method of claim 8, wherein the monitoring comprises thermally monitoring the detection medium by acquiring infrared images of the test specimen and detection medium.

10. The method of claim 8, wherein the detection medium is substantially removed from an area surrounding the surface discontinuity prior to application of the action reacting medium, and the reacting medium is applied to an area including both the surface discontinuity and the area surrounding the surface discontinuity.

11. The method of claim 8, wherein the discontinuity comprises a crack in the surface of the test specimen and the detection medium comprises a liquid detection medium that enters the crack through capillary action.

* * * * *